United States Patent [19]

Schlosberg et al.

[11] 4,161,689
[45] Jul. 17, 1979

[54] METHOD AND APPARATUS FOR REPAIRING PROTECTIVELY LINED REACTOR VESSELS

[75] Inventors: Seymour Schlosberg, East Brunswick; Michael J. Lerman, Carteret, both of N.J.

[73] Assignee: DeDietrich (USA), Inc., Union, N.J.

[21] Appl. No.: 900,124

[22] Filed: Apr. 26, 1978

Related U.S. Application Data

[60] Continuation of Ser. No. 820,918, Aug. 1, 1977, Pat. No. 4,112,572, which is a division of Ser. No. 663,113, Mar. 2, 1976, Pat. No. 4,078,697.

[51] Int. Cl.² .......................................... G01R 31/12
[52] U.S. Cl. ..................................................... 324/54
[58] Field of Search ........................... 324/29, 30, 54; 85/1 JP, 1 R; 29/401; 52/514

[56] References Cited

U.S. PATENT DOCUMENTS

| 2,631,360 | 3/1953 | Sanford et al. | 29/401 |
| 2,824,663 | 2/1958 | Fischer | 85/1 JP |
| 2,890,845 | 12/1959 | Kiekhaefer | 85/1 R |
| 2,917,819 | 12/1959 | Britton et al. | 29/401 |
| 3,236,407 | 2/1966 | Zelman et al. | 29/401 |
| 3,440,707 | 4/1969 | Warren et al. | 52/514 |
| 3,555,414 | 1/1971 | Deichélmann | 324/54 |
| 3,803,972 | 4/1974 | Deutsher | 85/1 JP |
| 3,831,085 | 8/1974 | Kravatil | 324/54 |
| 3,858,114 | 12/1974 | Voellminn et al. | 324/54 |
| 3,863,146 | 1/1975 | Ehret | 324/54 |
| 3,965,415 | 7/1976 | Ehret | 324/54 |
| 4,078,697 | 3/1978 | Schosberg et al. | 29/401 R |
| 4,080,561 | 3/1978 | Thompson | 324/54 |

*Primary Examiner*—Samuel W. Engle
*Assistant Examiner*—S. A. Cangialosi
*Attorney, Agent, or Firm*—Pennie & Edmonds

[57] ABSTRACT

Breaks in the lining of a protectively lined reactor vessel are repaired without introducing unwanted electrical paths through the vessel. Specifically, the breaks are repaired using a plug comprising an insulated anchor stud anchored into the portion of the metal support wall underlying the break; a sealing gasket disposed on the portion of the protective lining surrounding the break; a washer disposed outside the sealing gasket; and a clamping arrangement mechanically coupling the washer and the anchor stud for clamping the gasket onto the protective lining throughout a path surrounding the break. In preferred embodiments, the insulating stud is a threaded cylindrical stud anchored into the wall by threading into a correspondingly threaded aperture, the sealing gasket is a corrosion-resistant, insulating plastic material such as a fluorocarbon, the washer is concave with respect to the gasket and filled with insulating cement, and the clamping arrangement is either a nut threadedly engaged to the insulating stud or a nut in combination with a second stud attached to the first. Reactor vessels using such repair plugs can utilize dip tubes of dissimilar metal without premature deterioration.

2 Claims, 6 Drawing Figures

METHOD AND APPARATUS FOR REPAIRING PROTECTIVELY LINED REACTOR VESSELS

This is a continuation, of application Ser. No. 820,918 filed Aug. 1, 1977 now U.S. Pat. No. 4,112,572 which is a division of application Ser. No. 663,113 filed Mar. 2, 1976, now U.S. Pat. No. 4,078,697.

BACKGROUND OF THE INVENTION

1. Field of the Invention

This invention relates to a method and apparatus for repairing protectively lined reactor vessels; and, more particularly, to a method and apparatus for repairing such vessels without introducing unwanted electrical paths through the vessel.

2. Description of the Prior Art

Protectively lined reactor vessels are widely utilized in chemical and allied industries to store a variety of corrosive and electrolytic materials such as aqueous solutions of acids, bases, and salts. These vessels typically comprise a conductive metal support wall, such as a steel shell, and an insulating protective inner lining such as glass, enamel, plastic, rubber, or the like. The metal wall provides the structural support required to hold the corrosive materials while the inner lining provides the corrosion resistance needed to protect the support wall from these materials.

Because of the importance of quickly repairing any break in the protective lining of a reactor vessel, such vessels are typically continuously monitored by electrical break detecting systems. Quick repair is of considerable importance in order to prevent destruction, by corrosion, of the underlying support wall. If the break is detected early, it can be readily repaired by the insertion of a corrosion resistant tantalum repair button. If, however, the break remains unnoticed for sometime, the support material may be substantially destroyed and a complete renewal of the protective lining by the manufacturer or even replacement of the vessel may be required.

The monitoring of a new vessel is relatively simple, but the subsequent insertion of tantalum repair buttons complicates the monitoring task by introducing electrical paths through the vessel. In a new vessel, breaks in the lining can be monitored by inserting an electrode into an electrolyte contained in the vessel and applying a potential difference between the electrode and the outer metal shell. A break is readily detected by the current flow resulting from the creation by the break of an electrical path through the insulating lining. Such breaks are typically repaired by the insertion of a tantalum screw or button therethrough and into the metal support wall.

Monitoring for and detection of subsequent breaks, however, is more complicated because the tantalum screw or button provides an unwanted electrical path from the electrolyte to the metal wall in which it is embedded. Consequently, any increased current flow due to a subsequent break might well be submerged in a high background level.

Prior methods for monitoring vessels thus repaired are less than completely satisfactory. One technique, disclosed in U.S. Pat. No. 3,555,414 issued to H. Deichelmann on Jan. 12, 1971, involves applying between the vessel wall and an electrode disposed in the electrolyte a direct current potential difference of such polarity that the wall is maintained at a positive potential with respect to the electrode. With such polarity and at appropriate magnitudes of voltage, the potential difference will effect a coating of the portion of the tantalum button exposed to the electrolyte with a thin passivating coating of tantalum oxide. This passivating coating, however, is readily subject to scratches and breakdown due to its very small thickness and, accordingly, does not permit reliable monitoring and detection.

An alternative technique disclosed in U.S. Pat. Nos. 3,831,085 and 3,858,114 issued to A. J. Kravatil and S. Voellmin, respectively, utilizes the natural "metal-to-metal" couple (battery effect) inherent with dissimilar metals disposed in electrolyte. In these techniques, an electrode of a metal other than steel, such as tantalum, is placed in the electrolyte. If a break in the lining should occur, a metal-to-metal couple is created between the steel and the metal electrode and a very sensitive galvanometer is used to detect the resulting current.

There are a number of difficulties with this alternative technique. First, the currents and voltages involved are very small and difficult to detect above background. Second, the technique is subject to spurious alarms because, in the normal use of such vessels it is common practice to insert into the electrolyte a variety of metal dip tubes which can activate the alarm system. Third, the frequent presence of the dissimilar metal dip tubes in the electrolyte contributes substantially to the deterioration of the tantalum plugs and the electrodes. This deterioration is the consequence of the generation of atomic hydrogen. Some of the atomic hydrogen permeates the tantalum, attacking it and causing embrittlement and cracking.

SUMMARY OF THE INVENTION

In accordance with the present invention, breaks in the lining of a protectively lined reactor vessel are repaired without introducing unwanted electrical paths through the vessel. Specifically, the breaks are repaired using a plug comprising an insulated anchor stud anchored into the portion of the metal support wall underlying the break; a sealing gasket disposed on the portion of the protective lining surrounding the break; a washer disposed outside the sealing gasket; and a clamping arrangement mechanically coupling the washer and the anchor stud for clamping the gasket onto the protective lining throughout a path surrounding the break. In preferred embodiments, the insulating stud is a threaded cylindrical stud anchored into the wall by threading into a correspondingly threaded aperture, the sealing gasket is a corrison-resistant, insulating plastic material such as a fluorocarbon, the washer is concave with respect to the gasket and filled with insulating cement and the clamping arrangement is either a nut threadedly engaged to the insulating stud or a nut in combination with a second stud attached to the first. Reactor vessels using such repair plugs can utilize dip tubes of dissimilar metal without premature deterioration.

BRIEF DESCRIPTION OF THE DRAWING

The advantages, nature, and various features of the present invention will appear more fully upon consideration of the illustrative embodiments now to be described in detail in connection with the accompanying drawing.

In the drawing.

For convenience of reference, identical elements are given the same reference numerals throughout the drawing.

DETAILED DESCRIPTION

Figure 1:
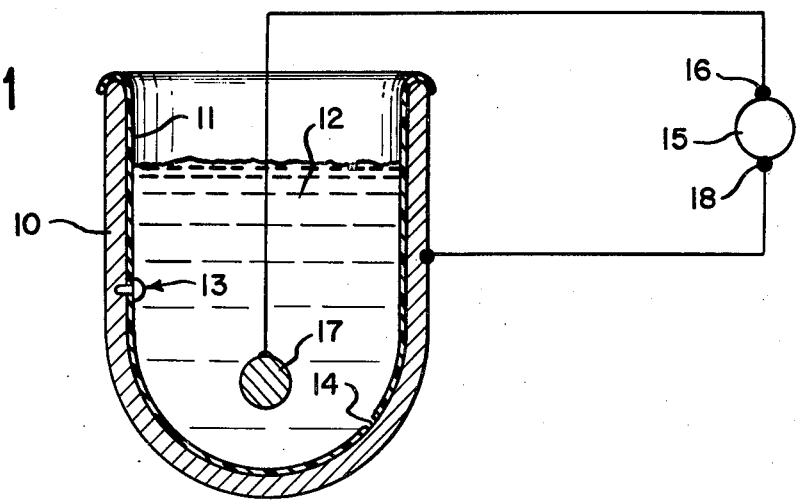
FIG. 1 is a schematic cross-sectional view of a typical protectively lined reactor vessel which has been repaired in accordance with the method and apparatus of the invention.

Referring to the drawing, FIG. 1 illustrates a typical protectively lined reactor vessel comprising a conductive metal support wall 10, typically made of steel, and an insulating protective inner lining 11, such as glass, enamel, plastic, rubber, or the like. The vessel is shown partially filled with a corrosive electrolytic reaction medium 12, such as an aqueous solution of an acid, base or salt. The vessel is shown with a break or fault in the protective lining repaired by repair plug 13 in accordance with the invention and with a second subsequently developed break 14.

Also illustrated is a sample monitoring and detection system useful for detecting breaks or faults in a vessel which has been repaired in accordance with the invention. The apparatus comprises, in substance, an ohmmeter 15 having one terminal 16 connected to electrode 17 disposed in the corrosive electrolytic medium 12 and the other terminal 18 electrically connected to conductive wall 10. Provided repair plug 13 does not introduce an electrical path through the vessel, subsequent break 14 can be readily detected by a substantial reduction in the resistance measured by ohmmeter 15.

Figure 2:
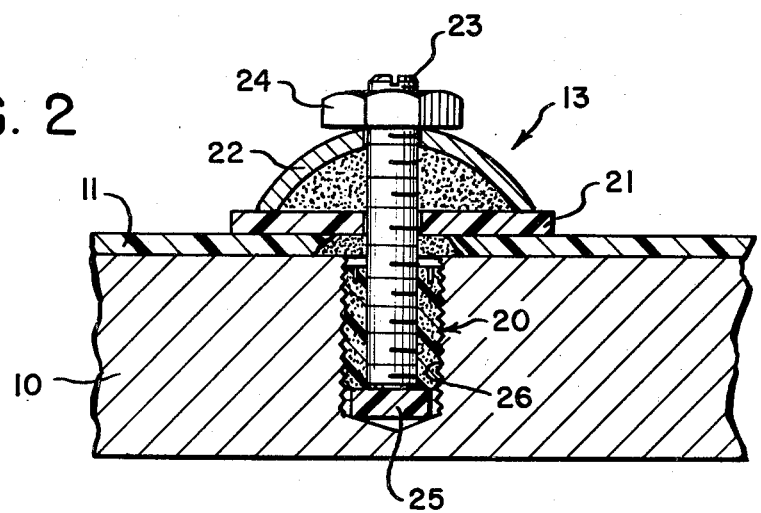
FIG. 2 is a schematic cross-sectional view of a portion of a reactor vessel wall which has been repaired, illustrating a preferred embodiment of a repair plug in accordance with the invention.

The repair plug 13 is shown in greater detail in FIG. 2. Specifically, this preferred embodiment of a repair plug comprises an insulated anchor stud 20 anchored into the portion of the metal support wall 10 underlying a break in the protective lining 11. In this specific embodiment, the stud 20 is a ceramic stud in the form of a threaded cylinder, and it is anchored by threading into a correspondingly threaded cylindrical aperture in wall 10. The ceramic can be any high strength, non-conducting ceramic such as, for example, an alumina, aluminum silicate, or magnesium silicate.

A sealing gasket 21 is disposed on the portion of the protective lining 11 surrounding the break. Preferably, the sealing gasket 21 is made of a corrosion-resistant, insulating plastic material such as a fluorocarbon, e.g., polytetrafluoroethylene. It may conveniently be in the form of an annular ring.

A clamping arrangement comprising washer 22, metallic stud 23, and nut 24 is provided for clamping gasket 21 onto protective lining 11 throughout a path surrounding the break. Preferably, washer 22 is a dish-shaped washer of tantalum or other corrosion-resistant metal with a concave surface facing the gasket so that pressure exerted on the washer is applied to the gasket around a path surrounding the break.

Metallic stud 23, which is preferably tantalum or other corrosion-resistant metal, is attached to anchor stud 20, preferably by threaded engagement. To this end, stud 23 is preferably a cylindrical threaded stud. Anchor stud 20 is provided with a correspondingly threaded aperture and an insulating element 25 such as a polytetrafluoroethylene disc or a ceramic cup is provided to insulate the inner end portion of metallic stud 23 from wall 10. Metal stud 23 extends through gasket 21 and washer 22.

The clamping arrangement is completed by nut 24, preferably tantalum. When nut 24 is threaded onto stud 23 and tightened down onto washer 22, pressure from the nut is transmitted to the gasket 21 along a path of contact surrounding the break in lining 11, thus sealing the underlying wall from corrosive electrolyte 12.

Advantageously, the space between the concave washer 22, the gasket 21, and the metal stud 23 is filled with a nonconducting, corrosion-resistant cement, such as a furan resin or a silicate cement. Similarly, the spaces between the gasket 21, the support wall 10, and the metallic stud 23 are filled with cement.

The method whereby a protectively lined reactor vessel is repaired in accordance with the invention can be illustrated in relation to the plug components shown in FIG. 2.

After the break is detected and after the preliminary step of removing corrosive liquid from the vessel, the first step in its repair involves producing an anchoring aperture 26 in the portion of the support wall 10 underlying the break. This aperture is expeditiously produced by drilling a sufficiently large diameter hole into but not through wall 10 to remove any corroded metal under the break and then preferably threading the drilled aperture.

The second step involves anchoring an insulating stud into the anchoring aperture just produced. In the preferred embodiment, this is accomplished by the preliminary step of placing insulating disc 25 into the aperture and then threading insulating stud 20 into the wall.

The third step involves disposing sealing gasket 21 on the portion of the protective lining 11 surrounding the break. As previously discussed, the gasket is preferably a corrosion resistant, insulating plastic material such as a fluorocarbon.

The fourth step involves applying a washer 22 outside the sealing gasket 21. Preferably, the washer is concave with respect to the gasket.

The fifth step involves applying between the washer 21 and the anchored stud 20 a clamping pressure for clamping the gasket 21 onto the protective lining 11 throughout a periphery surrounding the break, thereby sealing the break. This clamping pressure is applied in the preferred embodiment by passing metal stud 23 through washer 22 and gasket 21 and threading it into anchor stud 20. Nut 24 is then threaded onto the stud 23, exerting a clamping pressure onto washer 22 which, in turn, clamps gasket 21 onto the lining 11 around the break. As a step preliminary to the insertion of metal stud 23, the space between the gasket 21 and the concave washer 22 and the space between the gasket 21 and support wall 10 can be filled with uncured insulating cement in order to produce a unitary insulating structure upon curing.

Alternatively, the metal stud 23 could be threaded into anchoring stud 20 prior to application of gasket 21 and washer 22. This approach, however, would make introduction of the insulating cement somewhat more difficult.

Figure 3:
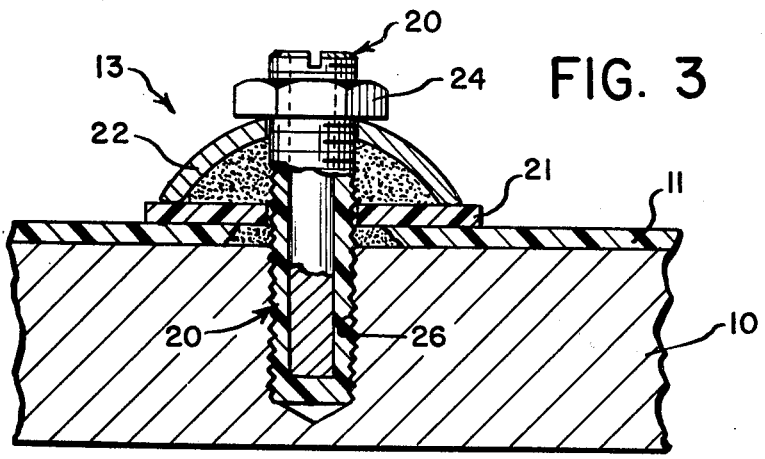
FIG. 3 illustrates a second embodiment of a repair plug in accordance with the invention.

FIG. 3 illustrates an alternative embodiment of a repair plug in accordance with the invention. This embodiment is similar to that shown in FIG. 2, except that insulating anchor stud 20 is elongated in comparison to that of FIG. 2, rendering unnecessary metal stud 23 and disc 25. In the preferred form, anchor stud 20 in this embodiment has a metal core to give it the necessary strength and an insulating outer layer of a strong insulating material such as a ceramic. In practice, this embodiment is particularly useful in repairing small breaks where little of the underlying wall has been corroded, and the embodiment of FIG. 2 is more useful in repairing breaks where the corrosion has spread to a greater extent.

The method for repairing a reactor vessel using the plug components shown in FIG. 3 is similar to the method using the plug components of FIG. 2 except that clamping is effected by threading nut 24 directly onto anchor stud 20.

Figure 4:
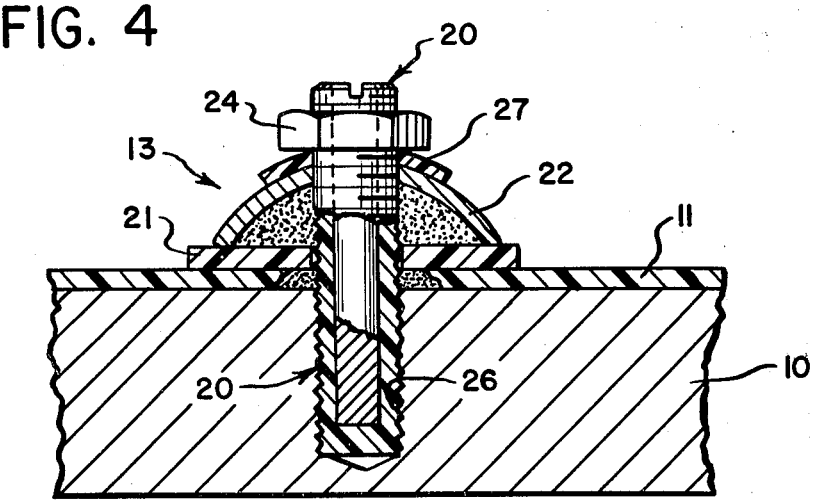
FIG. 4 illustrates a third embodiment of such a repair plug.

FIG. 4 illustrates a second alternative embodiment of a repair plug in accordance with the invention. This embodiment is similar to that shown in FIG. 3, except that a secondary insulating gasket 27 is disposed between nut 24 and washer 22. Such a gasket provides yet a further level of insulation and sealing between the interior of the vessel and the metal wall.

Figure 5:
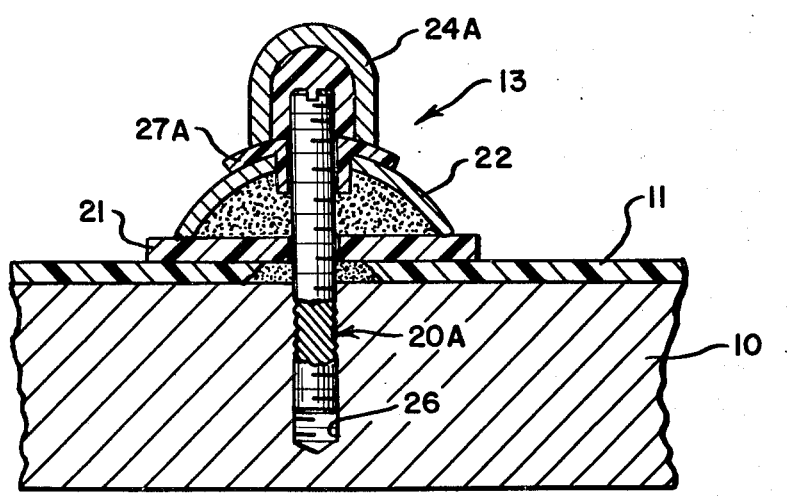
FIG. 5 illustrates a fourth embodiment of such a repair plug.

FIG. 5 illustrates a repair plug in accordance with a second aspect of the invention wherein the anchor stud 20A is conductive rather than insulating, but is electrically insulated from the electrolyte by an insulating cap nut 24A in cooperation with a second insulating gasket 27A. Preferably, the anchor stud 20A is tantalum or other corrosion-resistant metal, the second gasket 27A is flanged for facilitating seal between the cap nut and the washer 22. The cap nut 24A is preferably a composite structure having a metal outer shell and an insulating inner section. This embodiment is useful for repairing breaks having a very small amount of corrosion as compared to the breaks where the embodiments of FIGS. 2 and 3 are particularly useful.

Figure 6:
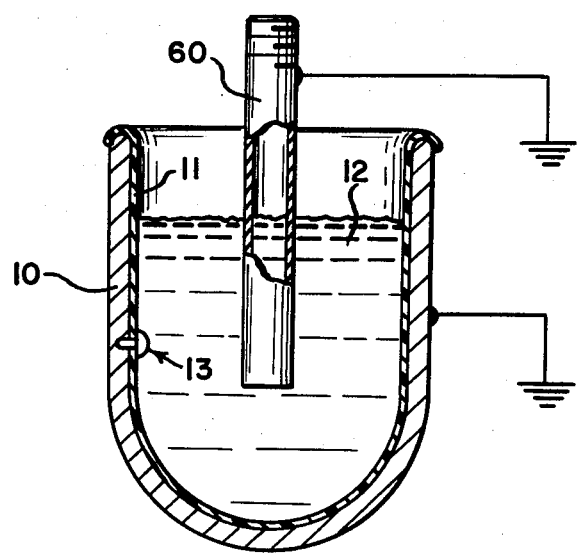
FIG. 6 is a schematic cross-sectional view of a protectively lined reactor including a repair plug in accordance with the invention and a dip tube of dissimilar metal.

FIG. 6 illustrates the combination of a protectively lined reactor vessel repaired in accordance with the invention and a dip tube 60 made of a metal different from the metal of the repair plug 13. Conveniently, the dip tube is a hollow cylindrical tube of a corrosion-resistant metal other than tantalum such as Hastelloy, a nickel-base alloy marketed by the Haynes Stellite Company. The repair plug 13 can be any one of the embodiments illustrated and described in connection with FIGS. 2-5, inclusive.

Since, in this combination, the reactor vessel has been repaired without introducing unwanted electrical paths through the lining, there is no substantial galvanic interaction between the repair plug and the dissimilar metal dip tube and hence no accelerated deterioration of either.

While the invention has been described in connection with only a small number of specific embodiments, it is to be understood that these embodiments are merely illustrative of the many possible specific embodiments which can represent applications of the principles of the invention. Thus, numerous and varied arrangements can be devised by those skilled in the art without departing from the spirit and scope of the present invention.

We claim:
1. In combination:
   a protectively lined reactor vessel for containing conductive liquid of the type comprising a conductive metal support wall and an insulating protective inner liner having at least one break therein;
   a repair plug disposed in the wall of said vessel, said repair plug comprising a first metal exposed to said conductive fluid and comprising, (a) an insulating anchor stud anchored into the portion of said metal support wall underlying said break, (b) a sealing gasket disposed on the portion of said protective lining surrounding said break and clamped onto said protective lining throughout a path surrounding said break, (c) a washer disposed upon said sealing gasket, (d) clamping means mechanically coupling said washer and said gasket onto said protective lining, and (e) means for insulating said anchor stud from the metal support wall; and
   break detection means comprising means for detecting a reduction in the electrical resistance between the conductive liquid contained in the interior of the vessel and the conductive metal support wall.
2. The combination according to claim 1 wherein said means for detecting a reduction in the electrical resistance between the conductive liquid contained in the interior of the vessel and the conductive metal support wall is comprised of a second metal which is disposed in said conductive liquid and is galvanically dissimilar to said first metal.

* * * * *